(12) United States Patent
Babaev

(10) Patent No.: US 7,729,779 B2
(45) Date of Patent: Jun. 1, 2010

(54) ELECTRODES FOR TRANSCUTANEOUS ELECTRICAL NERVE STIMULATOR

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 824 days.

(21) Appl. No.: 11/393,454

(22) Filed: Mar. 29, 2006

(65) Prior Publication Data

US 2007/0239250 A1    Oct. 11, 2007

(51) Int. Cl.
*A61N 1/04* (2006.01)
*A61N 1/18* (2006.01)

(52) U.S. Cl. .................. 607/115; 607/116; 607/152; 607/155

(58) Field of Classification Search ............ 607/2, 607/115, 152, 155
See application file for complete search history.

(56) References Cited

U.S. PATENT DOCUMENTS

| 3,979,646 | A | | 9/1976 | Peche et al. | |
|---|---|---|---|---|---|
| 4,427,920 | A | | 1/1984 | Proud et al. | |
| 4,736,752 | A | * | 4/1988 | Munck et al. | 607/152 |
| 4,784,161 | A | * | 11/1988 | Skalsky et al. | 607/116 |
| 4,938,231 | A | * | 7/1990 | Milijasevic et al. | 607/129 |
| 4,973,809 | A | | 11/1990 | Jenkins | |
| 5,191,901 | A | * | 3/1993 | Dahl et al. | 607/129 |
| 2006/0167527 | A1 | * | 7/2006 | Femano et al. | 607/50 |

\* cited by examiner

*Primary Examiner*—Carl H Layno
*Assistant Examiner*—Natasha N Patel

(57) ABSTRACT

A transcutaneous electric nerve stimulator (TENS) electrode that comprises a conductive layer containing both an inner perimeter(s) and an outer perimeter(s) is disclosed. When used with TENS treatment protocols and devices or other treatment/therapy methods, the electrode can induce a higher rate of A fiber firing by creating baffling to balance the electrical current flowing through the electrodes and induces superior analgesia.

7 Claims, 3 Drawing Sheets a)

b)

a)

b)

ELECTRODES FOR TRANSCUTANEOUS ELECTRICAL NERVE STIMULATOR

BACKGROUND OF THE INVENTION

1. Field of the Invention

The present invention relates to a Transcutaneous Electric Nerve Stimulator (TENS) electrode that comprises a conductive layer containing both an inner perimeter(s) and an outer perimeter(s).

2. Description of the Related Art

The conscious perception of pain involves the transmission of sensory information across three primary types of neurons that form a pathway from the body to the brain. Responding directly to the painful stimulus, peripheral afferent fibers transmit a message indicating the presence of pain to intermediate neurons in the dorsal horn of the spinal cord. Acting as middlemen, intermediate neurons in the dorsal horn receive the message of pain from peripheral fibers and relay it to spinal cord neurons projecting to the brain, where the pain is consciously perceived.

Two types of peripheral afferent fibers respond directly to painful stimuli. Fast conducting A fibers respond to the immediate presence of pain, such as a prick or a burn. The activation of A fibers generally elicits a withdraw reflex. Slow conducting C fibers are responsible for the perception of persistent, sustained, lingering pain. Unlike A fibers that respond fast and turn off quickly, C fibers are slow to respond and continue to respond after the painful stimulus is removed.

The gate control theory of Mazack, R. & Wall, P. D. (1965) Pain mechanisms: a new theory. *Science,* 150, 971-979, proposes that dorsal horn neurons act as a gate increasing or decreasing the transmission of nerve impulses from peripheral fibers to spinal cord neurons projecting to the brain. Decreasing the responsiveness of dorsal horn neurons to C fiber stimulation will retard or prevent dorsal horn neurons from passing on the message of pain perception from C fibers to spinal neurons projecting to the brain. This will prevent the brain from becoming aware of the presence of persistent, sustained, lingering pain thereby providing an analgesic effect against persistent, sustained, lingering pain.

Reducing a neuron's responsiveness to stimulation can be accomplished by the induction of long term depression (LTD). LTD is a cellular phenomenon in which a neuron's sensitivity to incoming stimulation decreases thereby requiring an increased level of stimulation to activate the neuron. Activating A fiber afferents leading to the dorsal horn with low frequency, low intensity stimulation induces LTD in dorsal horn neurons to C fiber stimulation. (Liu, X. G., Morton, C. R., Azkue, J. J., Zimmermann, M., & Sandkühler, J. (1998) Long-term depression of C-fibre-evoked spinal field potentials by stimulation of primary afferent Aδ-fibres in the adult rat. *European Journal of Neuroscience,* 10, 3069-3075.) Activating A fiber afferents leading to the dorsal horn with high frequency, low intensity stimulation produces a more reliable and stable LTD in dorsal horn neurons to C fiber stimulation. (Ikeda, H., Asai, T., & Murase, K. (2000) Robust changes of afferent-induced excitation in the rat spinal dorsal horn after conditioning high-frequency stimulation. *Journal of Neurophysiology,* 83, 2412-2420 and Liu, X. G., Morton, C. R., Azkue, J. J., Zimmermann, M., & Sandkühler, J. (1998) Long-term depression of C-fibre-evoked spinal field potentials by stimulation of primary afferent Aδ-fibres in the adult rat. *European Journal of Neuroscience,* 10, 3069-3075.)

High and low frequency, low intensity stimulation that activates A fiber afferents stimulates the release of endogenous opiates that are critical for the induction of LTD in dorsal horn neurons to C fiber stimulation. Administering low doses of Nalaxone, an opiate receptor blocker, inhibits low frequency, low intensity stimulation induced LTD, but not high frequency, low intensity stimulation induced LTD. (Ikeda, H., Asai, T., & Murase, K. (2000) Robust changes of afferent-induced excitation in the rat spinal dorsal horn after conditioning high-frequency stimulation. *Journal of Neurophysiology,* 83, 2412-2420.) High dose Nalaxone inhibits high frequency, low intensity stimulation induced LTD. (Ikeda, H., Asai, T., & Murase, K. (2000) Robust changes of afferent-induced excitation in the rat spinal dorsal horn after conditioning high-frequency stimulation. *Journal of Neurophysiology,* 83, 2412-2420.) These findings imply that the release of opiates is critical for the induction of LTD in dorsal horn neurons and that the level of opiate release is positively correlated with the firing frequency of A fiber afferents.

The administration of opiates and opiate derivatives is considered the gold standard for managing persistent, lingering, sustained pain. However, the use of these compounds is severely limited by the development of tolerance and addiction in patients. Through continued use of opiates and opiate derivatives, patients develop a tolerance or loss of analgesic efficacy, requiring the administration of higher doses to produce the necessary level of analgesia. However, patients do not develop tolerances to the toxic effects of opiates and opiate derivatives, such as respiratory depression. Thus, continued use of opiates and opiate derivatives will eventually place the patient in a situation where the dose required to produce sufficient analgesia is lethal. Consequently, the prolonged use of opiates to manage pain is not possible. Therefore, there is a need for a pain management strategy that utilizes the efficacy of opiates and avoids the development of tolerance and addiction.

Within the above mentioned LTD paradigms, electrical stimulation was applied directly to the portion of the A fiber afferents located within the dorsal horn of the spinal chord. The rate of firing of stimulated A fiber afferents was controlled by the frequency of stimulation, with the higher the frequency of stimulation, the higher the rate of firing. The selective activation of A fiber afferents was controlled by the intensity of stimulation. Low intensity stimulation selectively activated A fiber afferents without activating C fiber afferents. The insertion of electrodes into the dorsal horn of patients suffering from persistent, sustained, lingering pain to stimulate a fast rate of A fiber afferent firing would be painful and impractical. Rather, noninvasive stimulation of A fiber afferents is preferred. TENS has been proven to be an effective, noninvasive treatment for the management of pain. TENS is believed to induce LTD in dorsal horn neurons to C-fiber stimulation by the activation of A fiber afferents. (Liu, X. G., Morton, C. R., Azkue, J. J., Zimmermann, M., & Sandkühler, J. (1998) Long-term depression of C-fibre-evoked spinal field potentials by stimulation of primary afferent Aδ-fibres in the adult rat. *European Journal of Neuroscience,* 10, 3069-3075.) The short lived analgesic effect induced by TENS treatment protocols and devices indicates that such protocols and devices induce low firing rates in A fiber afferents. Accordingly, there is a need for a TENS treatment protocol and device that induces a higher rate of firing in A fiber afferents to produce a longer lived analgesia in patients suffering from persistent, sustained, lingering pain.

SUMMARY OF THE INVENTION

The use of an electrode containing a conductive layer containing both an inner perimeter(s) and an outer perimeter(s) with TENS protocol and devices can induce a higher rate of A fiber afferent firing by balancing the electrical current flowing through the electrodes as to create baffling. Electrodes used in TENS treatment protocols and devices function as capacitor plates that transmit an electrical current across skin to stimulate A fiber afferents. Skin has natural impedance to the flow of electrical current. Because the flow of electrical current always follows the path of least impedance, the electrical current flow is unevenly distributed across the electrode plates, with the higher concentration of electrical current flowing at points where the electrode plates are at their closest. Therefore, the A fiber afferents with dendrites along the shortest path between the electrodes are stimulated with increased energy/electrical current while many of the A fiber afferents with dendrites along longer pathways do not receive sufficient stimulation.

Electrode plates containing a conductive layer containing both an inner perimeter(s) and an outer perimeter(s) have the effect of balancing the impedance between A fiber afferents with dendrites along the shortest paths with A fiber afferents having dendrites along longer pathways, resulting in a balance of electrical current distribution. This serves to both protect short pathway A fiber afferents from over stimulation as well as ensuring long pathway A fiber afferents receive the sufficient amount of stimulation needed to fire. The increased number of A fiber afferents with proper stimulation thus produces a greater rate of A fiber afferent firing within the dorsal horn of the spinal cord. The resulting higher rate of A fiber afferent firing within the dorsal horn of the spinal cord will produce a more stable and persistent LTD in response to C fiber stimulation, increasing the level of analgesia produced to persistent, sustained, lingering pain.

One aspect of the invention may be to provide an electrode producing superior analgesia when used with TENS treatment protocols and devices as well as other treatment/therapy methods.

Another aspect the invention may be to provide an electrode producing superior retraining of muscles when used with TENS treatment protocols and devices as well as other treatment/therapy methods.

Another aspect of the invention may be to provide an electrode that reduces the amount of the current required to elicit medical effects such as, but not limited to, the induction of analgesia and the retraining of muscles when the electrode is used with TENS treatment protocols and devices as well as other treatment/therapy methods, thereby improving patient comfort and tolerance of the procedure.

Another aspect of the invention may be to provide an electrode that reduces the amount of current required to elicit medical effects such as, but not limited to, the induction of analgesia and the retraining of muscles when the electrode issued with TENS treatment protocols and devices as well as other treatment/therapy methods, thereby allowing the construction of smaller and more portable treatment/therapy devices than currently exist.

These and other aspects of the invention will become more apparent from the written descriptions and figures below.

BRIEF DESCRIPTION OF THE DRAWINGS

The present Invention will be shown and described with reference to the drawings of preferred embodiments and clearly understood in details.

DETAILED DESCRIPTION OF THE INVENTION

The basic construction of electrodes for use in Transcutaneous Electric Nerve Stimulation (TENS) is well known in the art and described and disclosed in detail in U.S. Pat. Nos. 4,934,383 (Olumac), 6,907,299 (Han), and 4,926,878 (Snedeker) herein included by reference. Though descriptive of the basic embodiment of a TENS electrode, the use of the present invention is not limited to those specific embodiments. An electrode of the present invention comprises a conductive containing at least one conductive area and at least one non-conductive area, at least one outer perimeter, and at least one inner perimeter.

Figure 1:
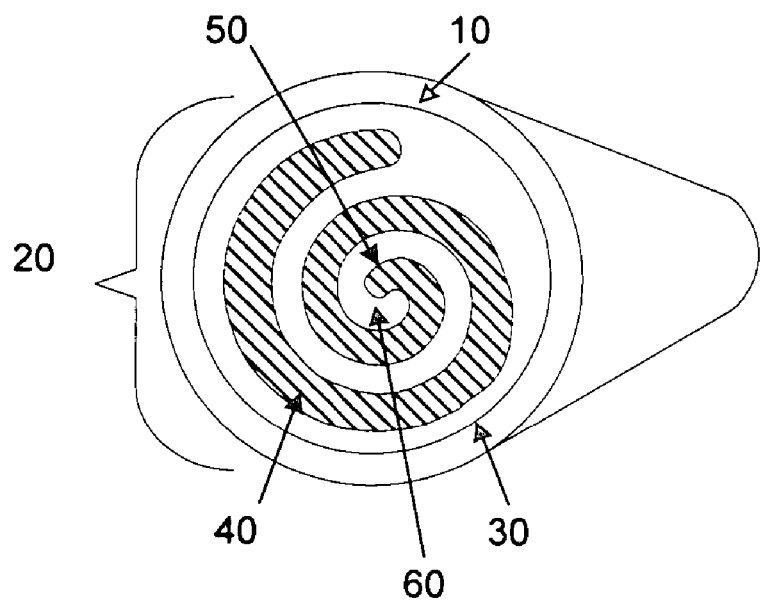
FIG. 1 are perspective views depicting the conductive layer of a TENS electrode in accordance with the present invention containing a spiral shaped inner perimeter.
Figure 1:
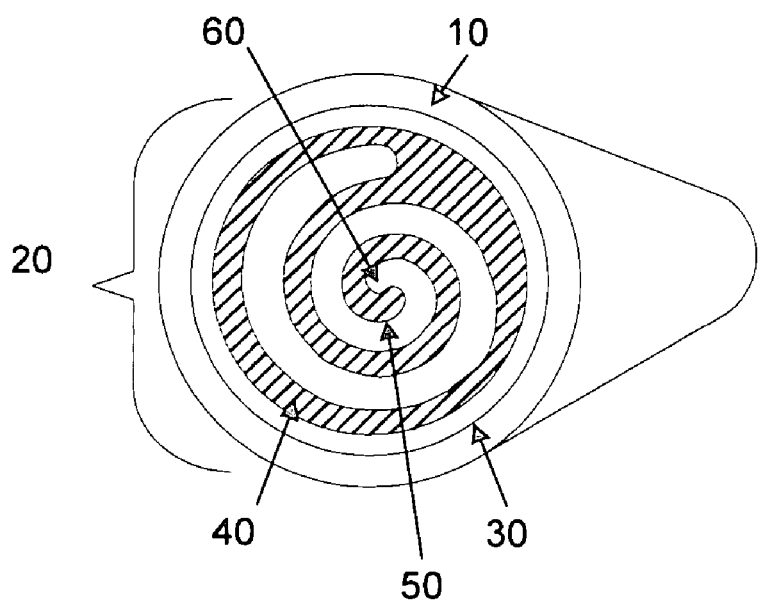

FIG. 1(a) depicts the conductive layer (10) of an electrode (20) of one embodiment of the present invention. The outer perimeter (30) is the boundary of the geometric region encompassing the conductive area (40) of the conductive layer (10). The inner perimeter (50) is the boundary of the area (60) within the outer perimeter (30) that contains the non-conductive area. The inner perimeter (50) in this electrode is in a spiral shape. However, other sizes or shapes of inner perimeters, or a combination thereof, may be utilized.

FIG. 1(b) depicts the conductive layer (10) of an electrode (20) of one embodiment of the present invention. The outer perimeter (30) is the boundary of the geometric region encompassing the conductive area (40) of the conductive layer (10). The inner perimeter (50) is the boundary of the area (60) within the outer perimeter (30) that contains the non-conductive area. The inner perimeter (50) in this electrode is in a spiral shape. This is the same shape of the electrode contained in FIG. 1(a) but with the conductive area and non-conductive area within the outer perimeter inverted.

Figure 2:
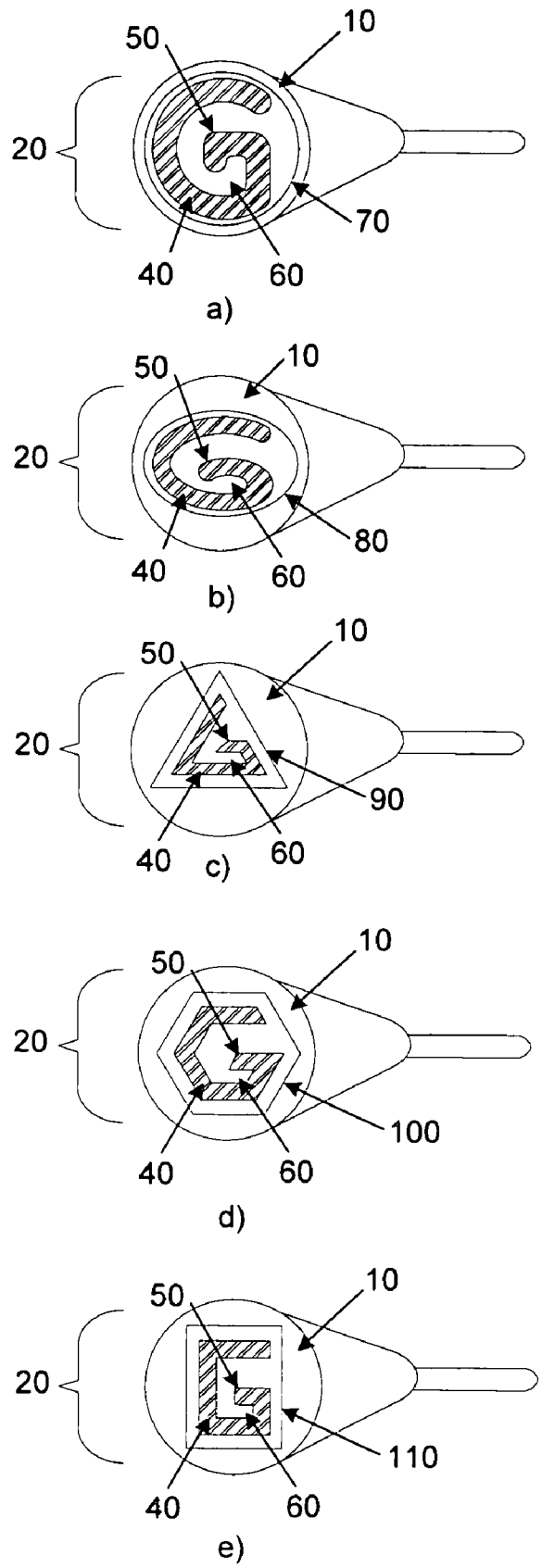
FIG. 2 is a perspective view depicting various geometric embodiments of the conductive area of a TENS electrodes in accordance with the present invention.

FIG. 2 depicts the conductive layers (10) of electrodes (20) constructed with outer perimeters (70, 80, 90, 100, 110) which encompass the conductive area (40), in which the outer perimeters are a circle (70), an ellipse (80), a triangle (90), a polygon (100), or a rectangle (110). Though a circular outer perimeter is preferred, different outer perimeters or combination of outer perimeters with other sizes, shapes, or a combination thereof may be utilized.

Figure 3:
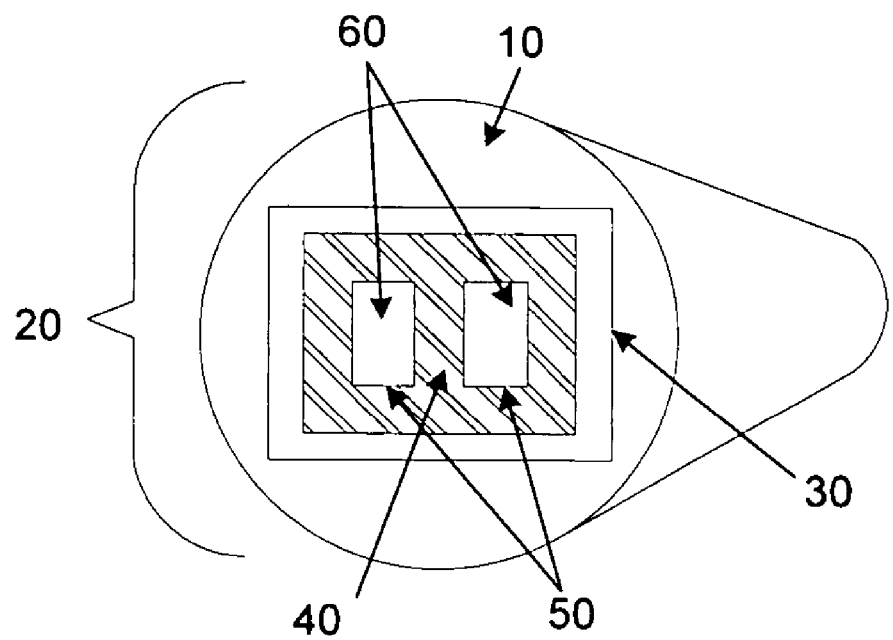
FIG. 3 is a perspective view depicting the conductive surface of a TENS electrode in accordance with the present invention containing a plurality of inner perimeters.

FIG. 3 depicts a conductive layer (10) of a mesh electrode (20) containing a plurality of inner perimeters (50) within the outer perimeter (30). A mesh electrode containing multiple inner perimeters can have inner perimeters of equal or varying sizes, shapes, or a combination thereof; furthermore, the number of inner perimeters can also be varied. The spatial arrangement of the inner perimeters in a mesh electrode can be ordered or any other type of arrangement.

Figure 4:
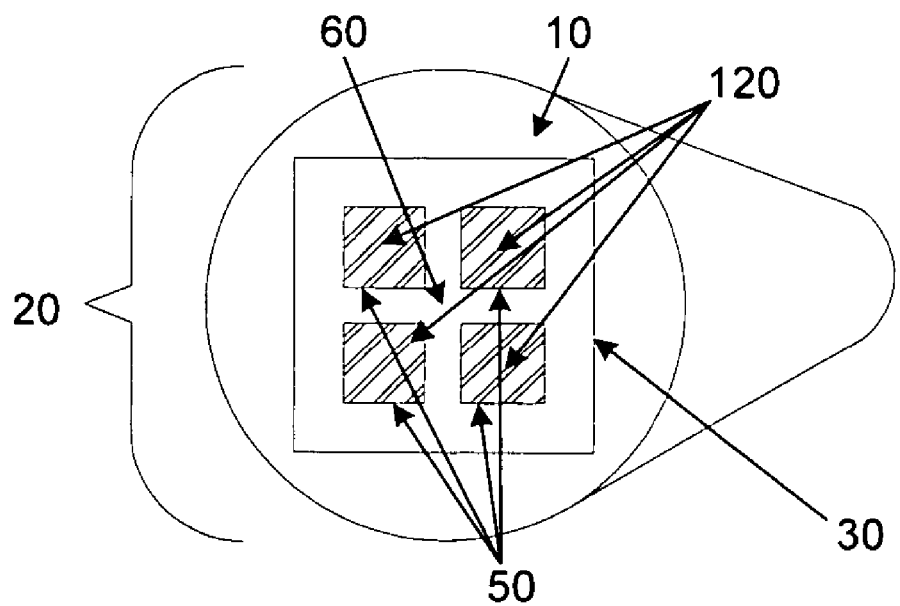
FIG. 4 is a perspective view depicting the conductive layer of a TENS electrode in accordance with the present invention containing a fragmented conductive area.

FIG. 4 depicts the conductive layer (10) of an electrode (20) containing a fragment conductive ara (120) within the outer perimeter (30) having inner perimeter (50). Other sizes, shapes, or a combination thereof and number of conductive surface fragments may be utilized.

The conductive area can be fashioned from a variety of conductive materials know to those skilled in the art, such as, but not limited to: tin, aluminum, silver or other metals; carbon fiber; an elastomeric material such as carbonized rubber or carbonized silicone (such material is manufactured and sold by Dow Corning under the name "Silastic"); inks containing electrical conductive particles such as graphite or metals (examples of such inks are "N-30" and "R-300" both or which are commercially available from Eeron, Inc. of Waltham, Mass.); conductive plastics; conductive gels; conductive liquids, or conductive adhesives, etc.

Though the preferred use of the present invention is for the administration of TENS, it may be utilized in other forms of treatments/therapy methods such as, but not limited to, interferential stimulation, biphasic stimulation, and Russian stimulation.

Furthermore, though the preferred use of the present invention is for the treatment of persistent, sustained, lingering pain it may also be utilized to elicit other clinical effects such as, but not limited to, inducing analgesia for surgical procedures and retraining muscles.

Although specific embodiments and methods of use have been illustrated and described herein, it will be appreciated by those of ordinary skill in the art that any arrangement that is calculated to achieve the same purpose may be substituted for the specific embodiments and methods shown. It is to be understood that the above description is intended to be illustrative and not restrictive. Combinations of the above embodiments and other embodiments as well as combinations of the above methods of use and other methods of use will be apparent to those having skill in the art upon review of the present disclosure. The scope of the present invention should be determined with reference to the appended claims, along with the full scope of equivalents to which such claims are entitled.

I claim:

1. An electrode for transcutaneous electrical nerve stimulation comprising: a conductive layer containing at least one conductive area and at least one spiral shaped non-conductive area; said conductive area being encompassed by at least one conductive outer perimeter and containing at least one conductive inner perimeter; and said inner perimeter containing said nonconductive area.

2. The electrode of claim 1, further characterized by said outer perimeter being a rectangle which encompasses said conductive area of said conductive layer.

3. The electrode of claim 1, further characterized by said outer perimeter being a circle which encompasses said conductive area of said conductive layer.

4. The electrode of claim 1, further characterized by said outer perimeter being an ellipse which encompasses said conductive area of said conductive layer.

5. The electrode of claim 1, further characterized by said outer perimeter being a triangle which encompasses said conductive area of said conductive layer.

6. The electrode of claim 1, further characterized by said outer perimeter being a polygon which encompasses said conductive area of said conductive layer.

7. The electrode of claim 1, further characterized by said conductive area being selected from the group consisting of metal, conductive plastic, conductive gel, conductive liquid, ink containing electrical conductive particles, and conductive adhesive.

* * * * *